United States Patent [19]
Klibansky

[11] 4,207,894
[45] Jun. 17, 1980

[54] PEDIATRIC SUCTION RECEPTACLE

[76] Inventor: Victoria A. Sinkel, 84 Shawsheen Rd., Pinehurst, Mass. 01866

[21] Appl. No.: 628,127

[22] Filed: Nov. 6, 1975

[51] Int. Cl.² ............................................. A61M 1/00
[52] U.S. Cl. ..................................... 128/276; 128/275
[58] Field of Search ................................ 128/275–277, 128/278, 2 F; 32/33; 23/252 R, 292, 259; 260/112.5 R

[56] References Cited
U.S. PATENT DOCUMENTS

| | | | |
|---|---|---|---|
| 3,362,400 | 1/1968 | DeBella | 128/2 F |
| 3,715,190 | 2/1973 | Park et al. | 23/252 R |

FOREIGN PATENT DOCUMENTS

| | | | |
|---|---|---|---|
| 444852 | 12/1927 | Fed. Rep. of Germany | 32/33 |
| 2035241 | 2/1972 | Fed. Rep. of Germany | 128/276 |

Primary Examiner—G. E. McNeil
Attorney, Agent, or Firm—James C. Wray

[57] ABSTRACT

A pediatric suction receptacle has a closed plastic collector with an upper wall integrally joined to a downward extending wall and an inward sloping wall terminating in a spigot. Two plastic tubes permanently connected to the upper wall have proximal ends extending into the chamber. Distal ends of the tubes have integrally formed two-way tubing adaptors. One tube is connected to a wall suction fitting, and the other tube is connected to a patient for receiving fluids to be calibrated.

9 Claims, 2 Drawing Figures

PEDIATRIC SUCTION RECEPTACLE

BACKGROUND OF THE INVENTION

Many receptor devices have been developed to aid physicians and nurses in collecting fluids from patients. Some of the devices have measurement graduation. Some employ suction to draw fluids from one position to another. However, at present, only devices which measure relatively large flows are available. Accurate measurement of smaller discharges is a critical necessity in pediatric intensive care units and after major heart and lung surgery in adults. The only way physicians and nurses can estimate such discharges now is to guess. No device is available or has been suggested which accurately measures every bit of discharge which flows from a patient.

Before preparing a patent application a search was conducted in records of the United States Patent and Trademark Office to determine whether prior art references showed or suggested such receptacles. The search was concentrated in Class 128, Surgery, Subclass 2F Fluid Collectors and Subclass 275 Receptors.

Examples of the most pertinent patents which were found are: U.S. Pat. Nos. 3,345,980; 3,362,400; 3,552,395; 3,742,934; and 3,871,230.

U.S. Pat. No. 3,552,395 shows a pediatric drainage receptor with initial small measurement.

U.S. Pat. No. 3,871,230 shows a fine calibration receptor with a fine flow bottom portion.

U.S. Pat. No. 3,742,934 shows a receptor with a sloped bottom for initial fine calibration.

U.S. Pat. No. 3,362,400 shows a fine calibration urine receptor with a valve at the bottom.

U.S. Pat. No. 3,345,980 shows a fine calibration receptor or urometer with a spigot at the bottom.

The several receptors found did not disclose measuring collectors which are suitable for measuring every drop of fluid which flows from a patient. No reference showed or suggested a suction receptor having a drainage fluid connection and a suction connection at the top with a fine calibration along the side and with a spigot at the bottom. No reference suggested a receptor formed with a solid top and permanently joined tubes.

One of the problems in the medical equipment which is related to the present invention is that often adaptors and tubes must be fitted together and that when the adaptors and tubes are fitted together, the possibility exists of creating leakage areas with loss of effectiveness of the device or with loss of fluid to be measured.

Another problem in related available devices and in disclosures of devices is that a possibility exists of losing fluid while the fluid is being decanted for measurement. Another inherent problem is that devices usually are joined with screw or bayonet threads at the top which increases the area for suction leakage or which requires removal of the receptor from the top for emptying. The entire operation is time consuming and creates a possibility of loss of accuracy in the collection process.

SUMMARY OF THE INVENTION

Briefly, the invention is a receptor for collecting and accurately measuring fluids from children. The receptor has a small container with a closed top and a funnel shaped bottom which is closed by a spigot. The container is calibrated in fine calibrations and holds 50 cc. of fluid. Two short one-eighth inch plastic tubes are permanently joined to the closed top of the plastic receptacle. Preferably two-way adaptors are formed on the ends of the short plastic tubes. A standard tube connects one adaptor with wall suction. A second tube connects the other adaptor to the patient. The device permits accurate measurement of fluid drained from a small child. No fluid passes without measurement.

The present device accurately measures minute amounts of fluid discharge from a body, which is a critical necessity in pediatric intensive care and after major heart and lung surgery in adults.

The devices of the present invention have been tried in test uses in a hospital's pediatric unit and have functioned successfully since November, 1974.

This device permits accurate measurement and obtaining of drainage specimens from an infant or small child. No drainage device made is able to accurately drain and measure fluid drained from an infant or small child.

This device is especially successful for a critically ill premature infant or any critically ill child where it is crucial to have an absolutely accurate measurement of drainage fluid.

The receptacle of the present invention comprises a plastic receptacle with a flat top wall joined to a cylindrical downward extending wall. A sloping wall joined to the bottom of the cylindrical wall leads to a narrow neck on which a spigot is mounted. Turning the spigot 90 degrees opens the bottom neck to drain the receptacle, and turning the spigot another 90 degrees closes the neck, sealing the receptacle. In a preferred form of the invention, the spigot is constructed with a spring so that the spigot is automatically turned to the closed condition upon being released. In one form of the invention, the spigot may be a rod which slides through a transverse cylindrical barrel in the narrow neck. One portion of the rod is solid. One portion of the rod has a transverse opening which may be aligned with the major vertical passageway of the neck for draining the receptacle. Pressing axially on one end of the spigot aligns the spigot opening with the neck passageway for draining the passage. Releasing the spigot permits a spring to slide the spigot back to its position which blocks the passageway.

In the turnable spigot a transverse opening in the spigot shaft is alignable with the passageway of the neck to drain the receptacle. A torsion spring may return the spigot against a stop to the closed position.

The vertical wall of the receptacle is calibrated in fine divisions up to the upper limit of 50 cubic centimeters.

Plastic tubes are connected to the upper wall and have proximal ends which extend through the upper wall into the receptacle. Distal ends of the plastic tubes have connection means which are adaptors for connecting the tubes to varied size suction and patient serving tubes, in completion of the apparatus of the invention.

The two-way adaptors which are the integrally mounted connection means permit the joining of the device with readily available wall suction jacks and with tubing leading to the portion of the patient from which fluids are collected. The absence of separate pieces insures the structural integrity of the apparatus and prevents collection loss due to leakage. Additionally, the integral construction permits the device to operate without suction losses, which would tend to give uneven readings of collection rates.

The integral construction of the present invention and the basal spigot drain insure that measured fluid may be withdrawn without interrupting the integrity of the equipment and without disassembling the equipment. The device may be drained while the collection process goes on or is interrupted for as brief a period of time as possible. The use of the spigot at the bottom permits the periodical draining or partial withdrawal of fluids from the receptacle with minimal interruption to the collections system.

One object of the invention is the provision of a pediatric suction receptacle apparatus comprising a small chamber having closed upper and lower ends having an upper wall and a downward extending wall permanently connected to the upper wall and having a spigot connected to the lower end of the chamber for emptying the chamber and having tubes connected to the upper wall and means connected to the tubes for connecting one of the tubes to a source of reduced pressure and another of the tubes to a source of patient's fluid.

Another object of the invention is the provision of a pediatric suction receptacle apparatus having closed upper and lower ends with an inward sloping wall connected to a lower end of a downward extending wall and with emptying spigot means connected to a narrow neck at a lower end of the downward sloping wall for controllably releasing fluid from the neck without disturbing the apparatus.

Another object of the invention is the provision of pediatric suction receptacle apparatus with a closed chamber with an emptying spigot connected to a lower end and with tubes permanently joined to a permanently closed upper end and having proximal ends of the tubes extending into the chamber for reinforcing and sealing the joints between tubes and the upper wall, whereby the chamber and tubes retain the closed structural integrity.

The invention has as another object the provision of a pediatric suction receptacle apparatus with a spigot-drained lower end and with a closed upper end with a suction tube and a patient fluid tube permanently connected to the upper end and with two-way tubing adaptors manufactured on distal ends of the tubes.

Another object of the invention is the provision of pediatric suction receptacle apparatus as described wherein the chamber ends, downward extending wall, tubes and two-way adaptors are uniformly constructed of a plastic material.

The invention has as a further object the provision of a pediatric suction receptacle apparatus which has a collection chamber with fine graduations up to 50 cubic centimeters.

These and further and other objects and features of the invention are apparent in the disclosure which includes the above and below specification with the claims and the drawing.

DETAILED DESCRIPTION OF THE DRAWINGS

Figure 1:
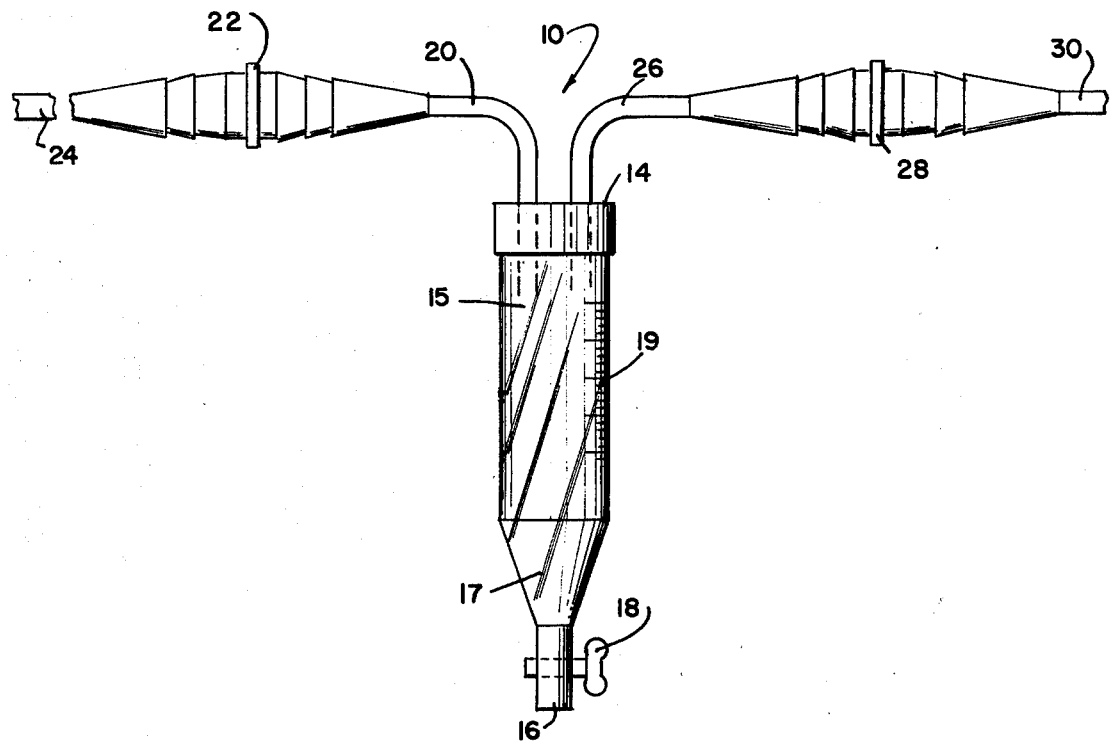
FIG. 1 is a side view of the pediatric suction receptacle of the present invention, showing the closed upper end, the tubes and adaptors permanently connected to the upper end and the lower end which is closed by a spigot.
Figure 2:
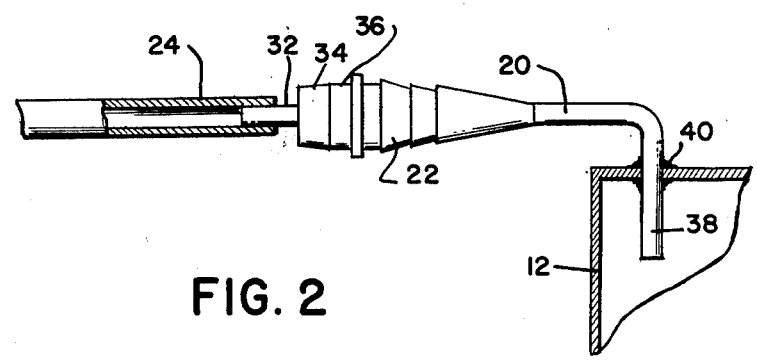
FIG. 2 is a detail of the tube and adaptor construction shown in FIG. 1.

Referring to FIGS. 1 and 2, the pediatric suction receptacle apparatus is generally referred to by the numeral 10. A chamber 12 is formed with closed upper and lower ends. A flat upper wall 14 has edges joined to a downward extending cylindrical wall 15. The lower end of the chamber terminates in a centrally located neck 16 with a central vertical passageway. A lower inward sloping wall 17 joins the lower end of cylindrical wall 15 and neck 16. Spigot 18 mounted in neck 16 controls the draining of the chamber.

One portion of the vertical wall 15 has fine calibrations 19 to indicate the amount of fluid in chamber 12.

A first tube 20 is permanently connected to the upper wall 14 such as shown in detail in FIG. 2. The distal end of tube 20 is formed as a multiple tubing adaptor 22. Suction tube 24 is connected to the adaptor and thus to the receptacle apparatus.

A similar tube 26 is similarly permanently connected to the upper wall 14. The tube 26 has a similar multiple tubing adaptor 28, which is manufactured integral with tube 26. Tube 30 is connected to adaptor 28 to carry fluids from the patient to the adaptor and to the receptacle.

Both tubes and adaptors are constructed similarly. As shown in FIG. 2, adaptor has steps 32, 34 and 36 which hold tubing of varied sizes. Thus the pediatric suction receptacle of the present invention can be used in hospital with any of several conventional sizes of suction tubes and fluid delivery tubes. As shown in the drawing, distal end 38 of tube 20 is inserted into the chamber, and welds 40 are formed around the tube to insure rigidity and structural integrity during use. The welds may be formed by bonding the materials with a separate bonding material or by heating the tube and upper wall 14 after assembly or by coating the elements with a quick drying chemical solvent to soften and fuse the elements during assembly.

While the invention has been described with reference to specific embodiments, it will be obvious to those skilled in the art that modifications and variations of the invention may be made without departing from the scope of the invention. The scope of the invention is defined in the following claims.

I claim:

1. Pediatric suction receptacle apparatus comprising a small chamber having closed upper and lower ends, an upper wall, a downward extending wall connected to the ends, and an emptying spigot means connected to the lower end of the chamber for releasing fluid from the lower end, first and second tubes having proximal ends connected to the upper wall for communication between the chamber and the tubes and first and second connection means mounted on distal ends of the respective first and second tubes for connecting the first tube to a source of reduced pressure and for connecting the distal end of the second tube to a source of patient's fluids, wherein the lower end of the small chamber further comprises a downward and inward sloping wall connected to a lower edge of the downward extending wall, and a downward extending neck connected to a lower edge of the downward and inward sloping wall, the neck having an interior passageway, and wherein the spigot means is mounted in the neck in selective blocking relationship to the passageway, whereby the passageway is closed and opened by the spigot means for closing and draining selectively the chamber.

2. The pediatric suction receptacle apparatus of claim 1 wherein the lower end further comprises a downward and inward sloping wall connected to a lower edge of the downward extending wall, and a downward extending neck connected to a lower edge of the downward and inward sloping wall, the neck having an interior passageway, and wherein the spigot means is mounted in the neck in selective blocking relationship to the passageway, whereby the passageway is closed and opened by the spigot means for closing and draining selectively the chamber.

3. The pediatric suction receptacle apparatus of claim 1 wherein the tubes are permanently joined to the upper wall.

4. The pediatric suction receptacle apparatus of claim 3 wherein the proximal ends of the tubes extend through the upper wall downward into the chamber.

5. The pediatric suction receptacle apparatus of claim 1 further comprising a series of fine graduations up to 50 cubic centimeters on the downward extending wall.

6. The pediatric suction receptacle apparatus of claim 1 wherein the connection means comprise multiple tubing adaptors integrally formed with the tubes.

7. The pediatric suction receptacle apparatus of claim 6 wherein the multiple tubing adaptors comprise two-way tubing adaptors manufactured with the tubes.

8. The pediatric suction receptacle apparatus of claim 1 wherein the receptacle walls and tubes are uniformly constructed of a plastic material.

9. The pediatric suction receptacle apparatus of claim 8 wherein the connection means are uniformly formed with the tubes of the plastic material.

* * * * *